(12) United States Patent
Rimmer

(10) Patent No.: US 9,975,668 B1
(45) Date of Patent: May 22, 2018

(54) MULTIPLE-LID CONTAINER

(71) Applicant: Alan C. Rimmer, Mechaniscburg, PA (US)

(72) Inventor: Alan C. Rimmer, Mechaniscburg, PA (US)

( * ) Notice: Subject to any disclaimer, the term of this patent is extended or adjusted under 35 U.S.C. 154(b) by 73 days.

(21) Appl. No.: 15/356,875

(22) Filed: Nov. 21, 2016

(51) Int. Cl.
| | |
|---|---|
| B65D 41/56 | (2006.01) |
| B65D 43/02 | (2006.01) |
| B65D 51/24 | (2006.01) |
| B65D 53/02 | (2006.01) |
| B65D 55/16 | (2006.01) |
| A01M 31/00 | (2006.01) |
| A61L 9/12 | (2006.01) |
| B65H 75/44 | (2006.01) |

(52) U.S. Cl.
CPC ......... *B65D 43/0225* (2013.01); *A01M 31/00* (2013.01); *A61L 9/127* (2013.01); *B65D 51/24* (2013.01); *B65D 53/02* (2013.01); *B65D 55/16* (2013.01); *B65H 75/4492* (2013.01)

(58) Field of Classification Search
CPC .. A01M 31/008; A01M 1/2055; A01M 29/12; A01M 1/2044
USPC ....................................................... 220/212
See application file for complete search history.

(56) References Cited

U.S. PATENT DOCUMENTS

| | | |
|---|---|---|
| 2,326,414 A | 8/1943 | Thompson |
| 2,836,323 A | 5/1958 | Robinson |
| 3,900,019 A | 8/1975 | Logiadis |
| 4,429,786 A | 2/1984 | Hucal |
| 4,600,111 A | 7/1986 | Brown |
| 4,865,207 A | 9/1989 | Joyner et al. |
| 5,002,179 A | 3/1991 | Dhalla |
| 5,947,379 A * | 9/1999 | Freeman ............. A01M 31/008 239/52 |
| 6,116,439 A | 9/2000 | Yaniv |
| 6,145,685 A | 11/2000 | Dick |
| 6,276,547 B1 | 8/2001 | Petryna |

(Continued)

FOREIGN PATENT DOCUMENTS

| | | |
|---|---|---|
| CA | 2356488 A1 | 10/2003 |
| CN | 204701902 | 10/2015 |
| CN | 205234530 | 5/2016 |

OTHER PUBLICATIONS

Scent Dripper Combo, Lyons Country Store, 2012-2016, p. 1-2.

(Continued)

*Primary Examiner* — Shawn M Braden
(74) *Attorney, Agent, or Firm* — McNees Wallace & Nurick LLC

(57) ABSTRACT

A multiple-lid container including a body having a passageway formed therein, the body having an open first end in fluid communication with the passageway, the passageway terminating at an opposed closed second end, the body and passageway forming an open-ended container. A first lid is securable to the first end to form a first closed container having a first chamber for holding a liquid. The first lid includes an applicator extending inside of the first chamber for wicking an amount of the liquid for applying the liquid on another surface when the first lid is removed from the first end. A second lid is operably secured to the open-ended container, the second lid is securable to the first end to form a second closed container. An elongate flexible member is secured to the first lid.

20 Claims, 2 Drawing Sheets

(56) References Cited

U.S. PATENT DOCUMENTS

| | | | |
|---|---|---|---|
| 6,648,239 B1* | 11/2003 | Myny | A01M 31/008 239/34 |
| 6,745,950 B1* | 6/2004 | Longo | A01M 31/008 239/145 |
| 7,643,735 B1* | 1/2010 | Mast | A01M 1/2077 222/146.5 |
| 8,113,364 B1 | 2/2012 | Asadi | |
| 8,365,941 B2 | 2/2013 | Mayer | |
| 9,028,383 B2 | 5/2015 | Carrasca et al. | |
| 9,370,598 B2* | 6/2016 | Kramer | A61L 9/12 |
| 9,675,724 B1* | 6/2017 | Ripka | A61L 9/12 |
| 2003/0024089 A1 | 2/2003 | Dziekonski | |
| 2006/0102585 A1 | 5/2006 | Richardson | |
| 2007/0181520 A1 | 8/2007 | Holley et al. | |
| 2007/0272698 A1 | 11/2007 | Brown et al. | |
| 2008/0035646 A1 | 2/2008 | Smith | |
| 2009/0124929 A1 | 5/2009 | Rossi-Pipitone et al. | |
| 2009/0266737 A1 | 10/2009 | Cole | |
| 2009/0290928 A1* | 11/2009 | Samuelson | A45F 5/004 401/6 |
| 2010/0308003 A1 | 12/2010 | Morrill et al. | |
| 2015/0060564 A1* | 3/2015 | Bowles | A61L 9/127 239/6 |
| 2017/0027158 A1* | 2/2017 | Slangan | A01M 31/008 |

OTHER PUBLICATIONS

The Buck Bomb Detonator Deer Scent Dispersal System, Bass Pro Shop, Sep. 7, 2016, p. 1-2.
Wildlife Research Center Magnum Scrape-Dripper, Gander Mountain, Sep. 7, 2016, p. 1.
Conquest Stink Stick EverCalm Scent Dispenser, Midway USA, p. 1.

* cited by examiner

US 9,975,668 B1

MULTIPLE-LID CONTAINER

FIELD OF THE INVENTION

The present invention is directed to the field of liquid containers, and more particularly, to liquid containers having multiple lids.

BACKGROUND OF THE INVENTION

Numerous activities involve the handling of pungent liquids. For example, deer hunters may utilize doe urine to act as an attractant, as well as a cover scent. Alternately or additionally, buck urine or oils secreted from the tarsal glands may also be used. In one technique, a hunter may use a drag line terminating in a mass of material onto which deer urine has been applied to spread the scent of the urine in the hunting area.

Unfortunately, during this process, which is typically performed in wooded areas, it can be difficult to avoid spilling this liquid or otherwise inadvertently contacting the liquid, that likewise permeates the hunter's person and gear, or both. This spillage may not only be undesirable for purposes of the hunt, but almost certainly is undesirable once the hunter returns home and needs to store the gear.

There is a need in the art for an improved apparatus that minimizes these shortcomings.

SUMMARY OF THE INVENTION

An embodiment is directed to a multiple-lid container including a body having a passageway formed therein, the body having an open first end in fluid communication with the passageway, the passageway terminating at an opposed closed second end, the body and passageway forming an open-ended container. A first lid is securable to the first end to form a first closed container having a first chamber for holding a liquid. The first lid includes an applicator extending inside of the first chamber for wicking an amount of the liquid for applying the liquid on another surface when the first lid is removed from the first end. The first lid forms a fluid tight seal with the first end of the first closed container. A second lid is operably secured to the open-ended container, the second lid securable to the first end to form a second closed container. The second lid forms a fluid tight seal with the first end of the second closed container, and an elongate flexible member is secured to the first lid.

A further embodiment is directed to a multiple-lid container including a cylindrical body having a passageway formed therein, the body having an open first end in fluid communication with the passageway, the passageway terminating at an opposed closed second end, the body and passageway forming an open-ended container. A first lid is threadedly securable to the first end to form a first closed container having a first chamber for holding a liquid, the first lid including an applicator extending inside of the first chamber for wicking an amount of the liquid for applying the liquid on another surface when the first lid is removed from the first end. The first lid forms a fluid tight seal with the first end of the first closed container. A second lid is operably secured to the open-ended container, the second lid threadedly securable to the first end to form a second closed container. The second lid forms a fluid tight seal with the first end of the second closed container. An elongate flexible member is secured to the first lid.

A further embodiment is directed to a method of handling a liquid including providing a body having a passageway formed therein, the body having an open first end in fluid communication with the passageway, the passageway terminating at an opposed closed second end, the body and passageway forming an open-ended container. The method further includes providing a first lid secured to the first end to form a first closed container having a first chamber for holding a liquid, the first lid including an applicator extending inside of the first chamber for wicking an amount of the liquid for applying the liquid on another surface when the first lid is removed from the first end. The method further includes providing a second lid operably secured to the open-ended container, the second lid securable to the first end to form a second closed container. The method further includes removing the first lid from the first end, securing the second lid to the first end, applying the liquid to a surface exterior of the first closed container with the applicator, removing the second lid from the first end, and securing the first lid to the first end.

Other features and advantages of the present invention will be apparent from the following more detailed description of the preferred embodiment, taken in conjunction with the accompanying drawings which illustrate, by way of example, the principles of the invention.

DETAILED DESCRIPTION OF THE INVENTION

The present invention provides a novel multi-lid container permitting convenient, unobtrusive handling of a liquid in the container, such as a pungent liquid.

The term "handling" in the context of "handling a liquid" refers to selectably applying the liquid on a surface with an applicator associated with a lid of the container, including instances in which the lid of the container may be separated from the container for extended periods of time.

The term "unobtrusive" in the context of "handling a liquid" refers to minimizing, if not preventing, spilling of the liquid in the container.

Figure 1:
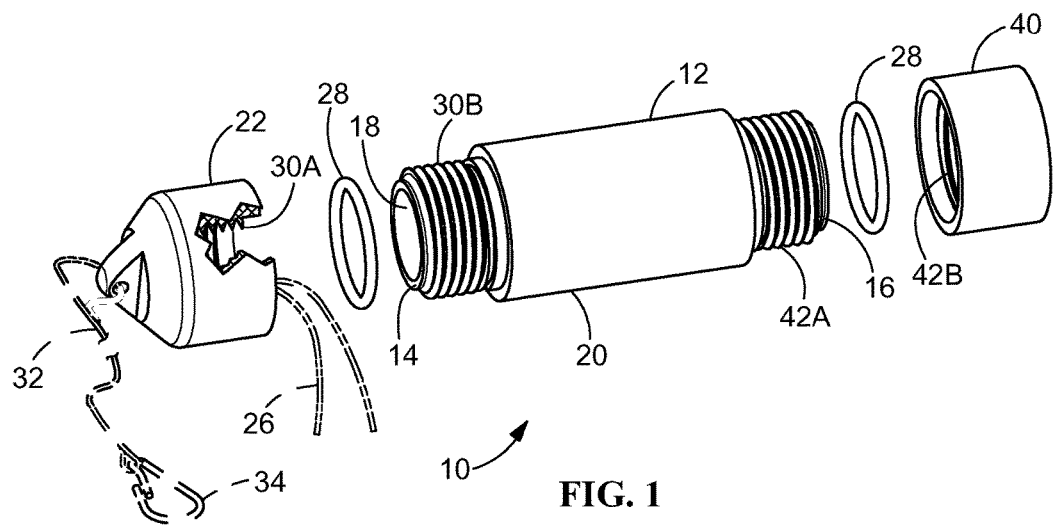
FIG. 1 is an exploded view of an exemplary multi-lid container.

Referring FIG. 1, a multi-lid container 10 includes a body 12 having an open end 14 and an opposed closed end 16. A passageway 18 is in fluid communication with end 14, the passageway terminating at closed end 16. Body 12 and passageway 18 forming or defining an open-ended container 20. As shown, open-ended container 20 is a cylinder. In one embodiment, open-ended container 20 is a non-cylinder. As further shown in FIG. 1, a lid 22 is adapted to receive end 14 of open-ended container 20, the lid and the container having corresponding securing features 30A, 30B. As shown, securing features 30A, 30B are mating screw threads. In one embodiment, securing features 30A, 30B can be mating quarter turn, quick-release features. In one embodiment, the securing features 30A, 30B form a clamping device, such as an over-center latch. In one embodiment, the securing features are magnets, such as when at least one of the lid and the body are ferromagnetic, or when magnets are secured to each of body 12 and lid 22. Any securing features may be used, so long as a fluid tight seal is established between body 12 and lid 22. The lid and body may be constructed of a suitable material that is corrosion-resistant to the liquid and environment and sufficiently strong to withstand use in harsh environments and conditions, such as metal, such as stainless steels, and non-metals.

The terms "body" and "open-ended container" may be used interchangeably.

Figure 2:
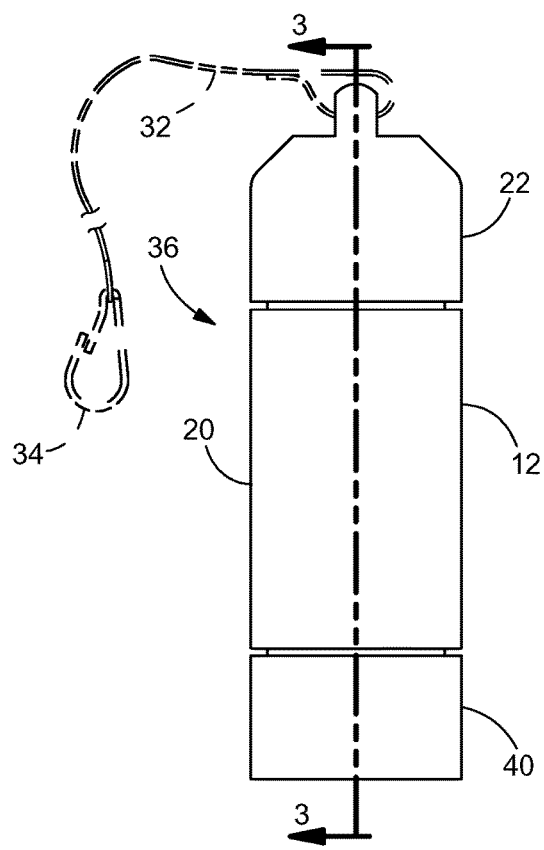
FIG. 2 is a side view of the assembled multi-lid container of FIG. 1.
Figure 3:
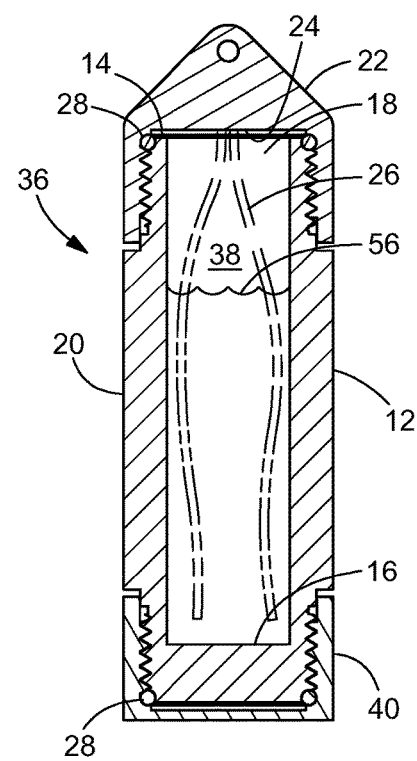
FIG. 3 is a cross-section of the multi-lid container taken along line 3-3 of FIG. 2.

As shown in FIGS. 1-3 to form a fluid tight seal, a seal 28 received by lid 22 is compressed between end 14 of body 12 and the lid. Securing lid 22 and body 12 together forms a closed container 36 having a chamber 38. Chamber 38 is defined by passageway 18, closed end 16 of body 12 and surface 24 of lid 22. Lid 22 includes an applicator 26 extending from surface 24 which is in contact with and wicks liquid 56 contained in chamber 38. As further shown in FIGS. 2-3, an end of lid 22 opposite body 12 is secured to a flexible member 32, permitting lid 22 to be dragged over a surface (not shown), with applicator 26 contacting the surface and applying an amount of liquid 56 onto the surface.

As further shown in FIGS. 1-3, a lid 40 is adapted to receive closed end 16 of open-ended container 20, the container and the lid having corresponding securing features 42A, 42B, similar to previously discussed securing features 30A, 30B. Preferably, a fluid tight seal is established between end 16 of body 12 and lid 40. To form a fluid tight seal, a seal 28 received by lid 40 is compressed between end 16 of body 12 and lid 40. Additionally, lid 40 is adapted to receive and form a fluid tight seal with end 14 of open-ended container 20 when lid 22 has been removed from end 14. Securing lid 40 and body 12 together forms a closed container 44 (FIG. 4) having a chamber 58 that is similar to closed container 36 for containing liquid 56 therein.

As described in FIGS. 1-4, multi-lid container 10 operates in the following manner, with the components initially arranged to form closed container 36. That is, fluid tight chamber 38 contains liquid 56 that is in contact with applicator 26. With closed container 36 oriented in a vertical position with lid 22 vertically above lid 40, lid 22 is removed from end 14 of open-ended container 20 by separating respective securing features 30A, 30B. Once lid 22 is removed from end 14, lid 40 is removed from end 16 of open-ended container 20 by separating respective securing features 42B, 42A. Lid 40 is then secured in a fluid tight manner to end 14 of open-ended container 20 to form closed container 44, such that liquid 56 is safely contained therein. Applicator 26 of lid 22 can then be brought into contact with another surface or surfaces, such as by dragging lid 22 by flexible member 32 for applying liquid 56 drawn into or wicked into the applicator. Optionally, it may be desirable to secure retention device 34 to an object, such as a tree limb, such that the scent of liquid 56 is permitted to emanate from applicator 26. By virtue of lid 40 being secured to open-ended container 20 to form closed container 44, liquid 56 is safely isolated and stored in chamber 58.

Once the application of liquid 56 by applicator 26 has been completed, lid 40 is removed from end 14 of open-ended container 20 and secured to end 16 of open-ended container 20. Once lid 40 has been secured to end 16, lid 22 and end 14 of open-ended container 20 are brought together, with applicator 26 being directed into passageway 18 of open-ended container, followed by securing lid 22 and end 14 together, forming closed container 36. At this point, liquid 56 is safely isolated and stored in chamber 38 of closed container 36, and surface 24 of lid 22, which may have been brought into contact with liquid 56, is similarly safely isolated by virtue of a fluid tight seal between lid 40 and end 16 of open-ended container 20.

Figure 4:
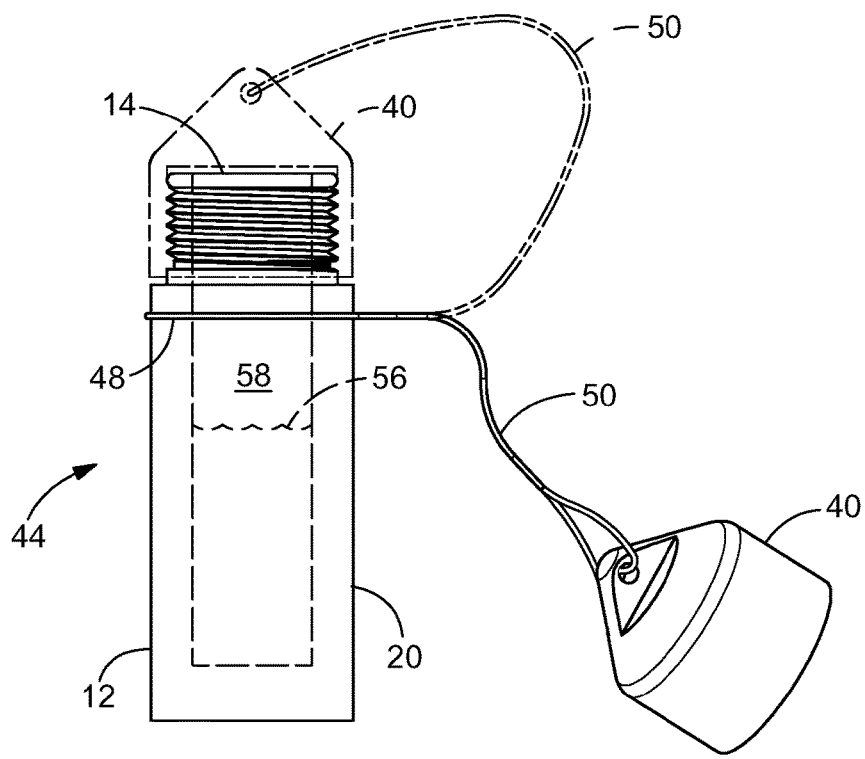
FIG. 4 is a side view of an exemplary multi-lid container.
Figure 5:
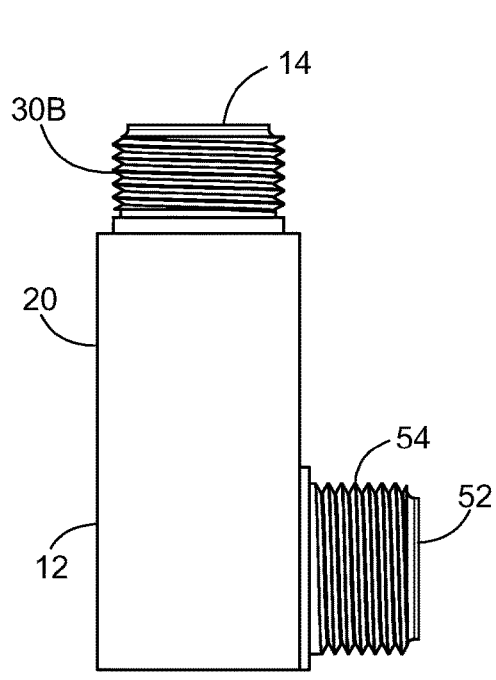
FIG. 5 is a side view of an exemplary container.

In one embodiment, as shown in FIG. 4, one end of a flexible member 50 is secured in a peripheral groove 48 formed in open-ended container 20, with the other end of flexible member 50 being secured to lid 40. As a result, upon removal of lid 22 from open-ended container 20, lid 40 is immediately available to be secured to end 14 of the open-ended container. Alternately, as shown in FIG. 5, open-ended container 20 can include a protrusion 52 having securing feature 54 for mating with corresponding securing feature 42B (FIG. 1) of lid 40. Protrusion 52 may be located at any suitable position on open-ended container.

Figure 6:
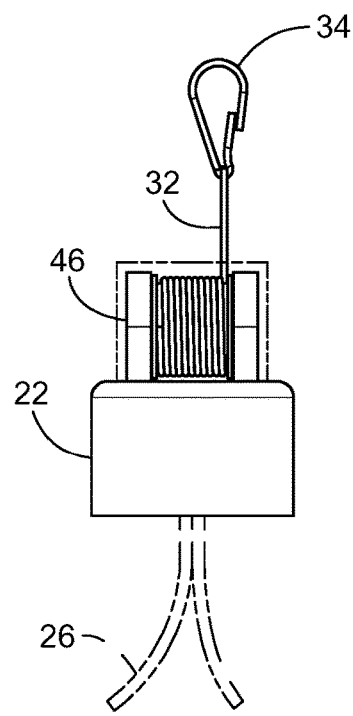
FIG. 6 is a side view of an exemplary lid.

In one embodiment, as shown in FIG. 6, lid 22 includes a collection device 46 for deploying/retracting flexible member 32. In one embodiment, collection device 46 is a reel that can be manually actuated, actuated by a motor, such as battery-powered electric motor, actuated by a torsion device, such as a spring, or other suitable arrangement.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A multiple-lid container, comprising:
   a body having a passageway formed therein, the body having an open first end in fluid communication with the passageway, the passageway terminating at an opposed closed second end, the body and passageway forming an open-ended container;
   a first lid securable to the first end to form a first closed container having a first chamber for holding a liquid, the first lid including an applicator extending inside of the first chamber for wicking an amount of the liquid for applying the liquid on another surface when the first lid is removed from the first end;
   wherein the first lid forms a fluid tight seal with the first end of the first closed container;
   a second lid operably secured to the open-ended container, the second lid securable to the first end to form a second closed container;
   wherein the second lid forms a fluid tight seal with the first end of the second closed container; and
   an elongate flexible member secured to the first lid.

2. The container of claim 1, wherein the first lid and the first end having corresponding securing features, and the second lid and the first end having corresponding securing features.

3. The container of claim 2, wherein the securing features comprises threads, quarter turn, quick-release features, magnets, and clamps.

4. The container of claim 1, wherein the first lid includes a collection device for deploying/retracting the flexible member.

5. The container of claim 4, wherein the collection device is a reel.

6. The container of claim 4, wherein the reel is manually actuated for deploying/retracting the flexible member.

7. The container of claim 4, wherein the reel is actuated by a torsion device for deploying/retracting the flexible member.

8. The container of claim 4, wherein the reel is actuated by a motor for deploying/retracting the flexible member.

9. The container of claim 1, wherein the open-ended container is a cylinder.

10. The container of claim 1, wherein an end of the flexible member opposite the first end includes a retention device.

11. A multiple-lid container, comprising:
- a cylindrical body having a passageway formed therein, the body having an open first end in fluid communication with the passageway, the passageway terminating at an opposed closed second end, the body and passageway forming an open-ended container;
- a first lid threadedly securable to the first end to form a first closed container having a first chamber for holding a liquid, the first lid including an applicator extending inside of the first chamber for wicking an amount of the liquid for applying the liquid on another surface when the first lid is removed from the first end;
- wherein the first lid forms a fluid tight seal with the first end of the first closed container;
- a second lid operably secured to the open-ended container, the second lid threadedly securable to the first end to form a second closed container;
- wherein the second lid forms a fluid tight seal with the first end of the second closed container; and
- an elongate flexible member secured to the first lid.

12. The container of claim 11, wherein the first lid includes a collection device for deploying/retracting the flexible member.

13. The container of claim 11, wherein the collection device is a reel.

14. The container of claim 13, wherein the reel is manually actuated for deploying/retracting the flexible member.

15. The container of claim 13, wherein the reel is actuated by a torsion device for deploying/retracting the flexible member.

16. The container of claim 13, wherein the reel is actuated by a motor for deploying/retracting the flexible member.

17. A method of handling a liquid, comprising:
- providing a body having a passageway formed therein, the body having an open first end in fluid communication with the passageway, the passageway terminating at an opposed closed second end, the body and passageway forming an open-ended container;
- providing a first lid secured to the first end to form a first closed container having a first chamber for holding a liquid, the first lid including an applicator extending inside of the first chamber for wicking an amount of the liquid for applying the liquid on another surface when the first lid is removed from the first end;
- providing a second lid operably secured to the open-ended container, the second lid securable to the first end to form a second closed container;
- removing the first lid from the first end;
- securing the second lid to the first end;
- applying the liquid to a surface exterior of the first closed container with the applicator;
- removing the second lid from the first end; and
- securing the first lid to the first end.

18. The method of claim 17, subsequent to securing the first lid to the first end, further comprises securing the second lid to the open-ended container.

19. The method of claim 17, subsequent to securing the second lid to the first end, further comprises deploying an end of an elongate flexible member away from the first lid.

20. The method of claim 19, subsequent to securing the first lid to the first end, further comprises retracting the end of the elongate flexible member toward the first lid.

* * * * *